United States Patent [19]

Shapiro

[11] 4,395,397

[45] Jul. 26, 1983

[54] APPARATUS AND METHOD FOR KILLING UNWANTED CELLS

[75] Inventor: Howard M. Shapiro, West Newton, Mass.

[73] Assignee: Sidney Farber Cancer Institute, Inc., Boston, Mass.

[21] Appl. No.: 303,141

[22] Filed: Sep. 17, 1981

[51] Int. Cl.³ .................. A61K 35/14; A61L 2/08; G21K 5/00
[52] U.S. Cl. .................. 424/101; 250/492.1; 356/36; 422/22; 424/95; 435/2; 435/7; 435/29; 435/173; 435/261; 435/289; 435/291; 435/311
[58] Field of Search .................. 422/21–25; 435/2, 3, 261, 289, 311, 813, 34, 29, 291, 173; 424/95, 101; 356/36, 39; 250/492.1

[56] References Cited

U.S. PATENT DOCUMENTS

| | | | |
|---|---|---|---|
| 3,817,703 | 6/1974 | Atwood | 422/22 |
| 3,826,364 | 7/1974 | Bonner et al. | 209/3 |
| 3,941,670 | 3/1976 | Pratt, Jr. | 422/22 X |
| 4,042,325 | 8/1977 | Tensmeyer | 21/54 R |

FOREIGN PATENT DOCUMENTS 2300677  7/1974  Fed. Rep. of Germany ........ 422/22

Primary Examiner—Arnold Turk

[57] ABSTRACT

Method and apparatus for removing, from a flowing liquid stream containing a suspension of living cells, a subpopulation of unwanted cells having one or more characteristics distinguishing them from the rest of the living cells. The method includes detecting the presence of the unwanted cells, generating signals in response to the presence of the unwanted cells, and providing pulses of laser light, in response to the generated signals, to impinge on and kill the unwanted cells.

4 Claims, 1 Drawing Figure

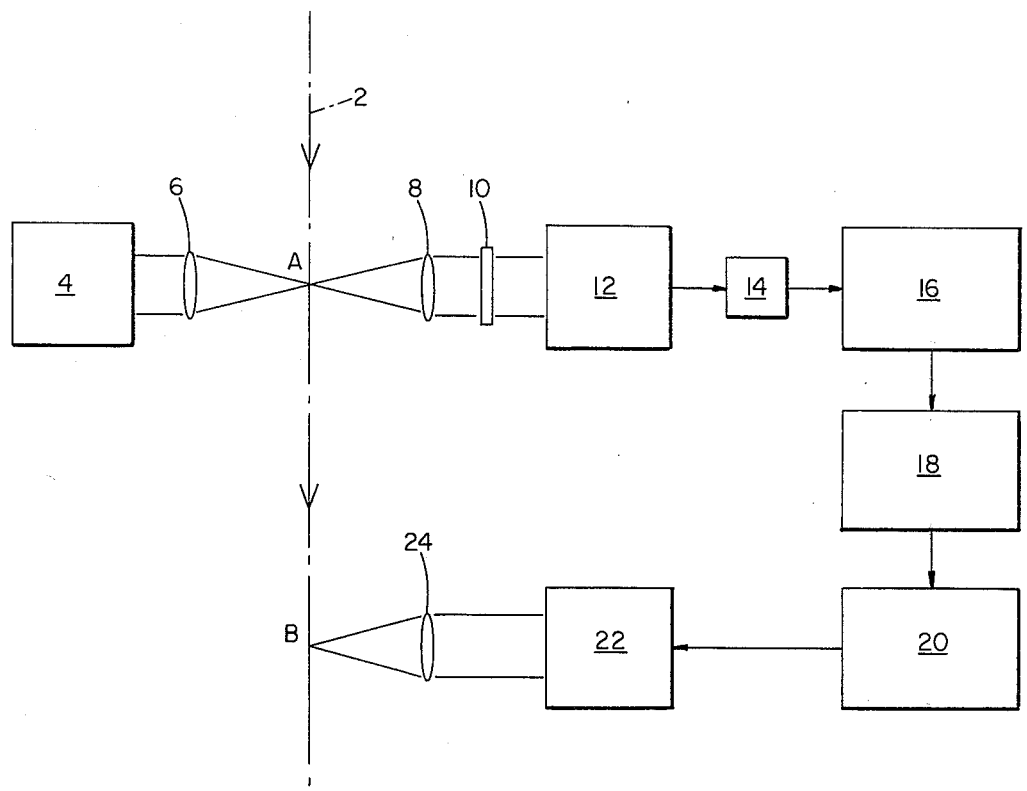

APPARATUS AND METHOD FOR KILLING UNWANTED CELLS

This invention relates to a method and apparatus for identifying and selectively destroying, within a population of living cells, a subpopulation of unwanted cells.

Cell separation methods, especially those in which cancerous cells are separated from normal cells, are widely described in the patent and non-patent literature. One such method, for example, is described in Bonner et al. U.S. Pat. No. 3,826,364, hereby incorporated by reference, in which cells, in a liquid stream, having a particular characteristic are made fluorescent, the flowing stream is broken into droplets, and fluorescent cells in the droplets are sensed using a laser and fluorometer. Droplets containing fluorescent cells are then electrically charged, and these charged droplets follow a different path from uncharged droplets; the cells in the stream are thus sorted according to whether they possess the particular characteristic.

It is also known that cells, e.g., microorganisms, can be killed by focusing a laser beam onto them. For example, in Tensmeyer U.S. Patent No. 4,042,325, there is disclosed a method for using a laser beam to kill microorganisms in a food container.

The method and apparatus of the present invention allow the removal of unwanted cells from a cell population not by sorting, but rather by killing them by means of laser light. This approach provides superior speed as well as reliability, and is particularly advantageous for the removal of cancer cells from a cell population.

The apparatus of the invention features means for detecting, in a flowing liquid stream containing a suspension of living cells, the presence of unwanted cells having one or more characteristics distinguishing them from other cells in the cell suspension; means for generating signals in response to the presence of the distinguishable cells; and means responsive to the signals for providing pulses of laser light to impinge on and kill the unwanted cells.

The liquid stream carrying the suspended cells preferably flows past a plurality of stations, one of which includes the detecting means and one of which, located farther downstream, includes the laser pulse generating means. The cells which are distinguished and killed are preferably cancer cells, which can be detected, e.g., by virtue of fluorescent antibodies specific to the cancer cells to be killed or, if the cells possess a detectable physical characteristic such as abnormally large size, by measuring a parameter such as light scattering, electrical impedance (the principal used in a Coulter counter), or acoustic properties. In addition, more than one cell characteristic can be measured, as is done, e.g., by multiparameter analyzers, which electronically measure both cell volume and the fluorescence of the DNA of labelled abnormal cells. If a light source is used in the detection method, the source can be a laser or a different conventional source such as an incandescent lamp.

The laser can be any high energy killing laser such as argon ion, neodymium YAG, krypton ion, or dye. The laser's continuous power output should be at least 10 watts and its pulse rate should be at least 30 kHz. Pulsed beam transmission can be achieved using pulsed operation or by using acoustic or optical modulation to lase and delase. The laser should generate light of a wavelength absorbed by cells; IR light is preferred, but UV and visible light are effective as well.

The liquid stream is preferably exposed directly to the laser beam, without the use of a window, and is preferably not broken into droplets, but maintained as a coherent stream.

The FIGURE of the drawing is a schematic diagram illustrating an embodiment of the invention.

The following specific example is intended to more fully illustrate the present invention, without acting as a limitation upon its scope.

EXAMPLE

In this example, the unwanted cells killed using the method of the invention are acute lymphoblastic leukemia cells. The method of the example takes advantage of the following chemotherapy concept, which has appeared in the literature.

Because chemotherapeutic agents used to treat leukemia are extremely toxic, it has been suggested that bone marrow cells be removed from a patient prior to treatment with such agents and stored in a viable state. The patient is then given a very high dose of the chemotherapeutic agent, sufficient to kill cancer cells remaining in the body, but also so high as to irreversibly damage any remaining bone marrow. Following treatment, the stored marrow is reinfused into the patient, allowing for regeneration of the blood cells and, hopefully, cure of the disease.

In order for this therapy to succeed, it is necessary that the marrow removed for retransplantation be free of cancer cells, or that cancer cells be removed from the marrow prior to reinfusion. Because approximately 100 million ($10^8$) cells must be given to the patient to reconstitute the bone marrow, the cell removal process must be rapid.

The method and apparatus of the invention can be used to effectively and quickly eradicate the cancer cells in the removed marrow. The first step in the method is to label the cancerous cells among the removed marrow cells using monoclonal antibody specific to human acute lymphoblastic leukemia antigen. The preparation of an appropriate monoclonal antibody is described in Ritz et al. (1980) Nature 283, 583. Fluorescein label is attached to the antibody using conventional techniques. The marrow cells, including both normal and labelled, cancerous cells, are then suspended in aqueous buffer.

Referring now to the drawing, the sensing means, including elements 2 to 18, is essentially as shown in the aforesaid Bonner et al. patent.

The cell suspension, in a narrow (50 $\mu$m–200 $\mu$m across) liquid stream 2, is directed to flow past blue argon low intensity laser 4, which is positioned to direct a beam at the cell stream at an angle 90° from the stream axis. Laser light passes through focusing lens 6 and then excites labelled cells in the stream, without killing them or the unlabelled cells, as the cells pass station A, to emit fluorescent radiation, which passes through object lens 8, filter 10, and into fluorometer 12, which includes a photomultiplier, and which detects the faint fluorescent pulses and transmits them to amplifier 14.

The amplified output from amplifier 14 is transmitted to single channel analyzer 16, which discriminates between signals of an intensity above and below a threshold level, and transmits signals above that value to adjustable gate pulse generator 18. This generator, which is gated to the velocity (1–20 m/sec) of the cell stream, delivers a pulse to laser trigger 20, which modulates high energy argon ion laser 22 (Control Laser Corp.) to emit a pulsed beam with a pulse duration ≦10 μ sec. The beam is sharply focused through lens 20, to the stream at station B, at the instant the cell which emitted the triggering pulse passes that point, so that each such cell is killed as it passes station B. The focal spot diameter is designed to be greater than the stream cross-sectional distance at point B; if the stream is 200 μm across, the focal spot diameter is adjusted to be about 300 μm or more.

This method allows approximately 60,000 cells per second to be passed by station B.

What is claimed is:

1. Apparatus for killing, in a flowing liquid stream containing a suspension of living cells, a subpopulation of unwanted cells having one or more characteristics distinguishing them from the rest of said living cells, said apparatus comprising means for detecting the presence of unwanted cells in a flowing stream containing a suspension of living cells, means for generating signals in response to the presence of said unwanted cells in said flowing stream, and means downstream from said detecting means and responsive to said generated signals, for providing pulses of laser light focused on said flowing stream to impinge on and kill said unwanted cells in said flowing stream.

2. A method for killing, in a flowing liquid stream containing a suspension of living cells, a subpopulation of unwanted cells having one or more characteristics distinguishing them from the rest of said living cells, said method comprising detecting the presence of unwanted cells in a flowing stream containing a suspension of living cells, generating signals in response to the presence of said unwanted cells in said flowing stream, and in response to said signals, providing pulses of laser light focused on said flowing stream to impinge on and kill said unwanted cells in said flowing stream.

3. The method of claim 2, wherein:

said unwanted cells are cancer cells, and said cancer cells are labelled with attached fluorescent antibody.

4. The method of claim 3, wherein:

said cancer cells are leukemia cells, and said antibody is a monoclonal antibody specific for said leukemia cells.

* * * * *